US00PP26264P2

(12) United States Plant Patent
Hartman

(10) Patent No.: US PP26,264 P2
(45) Date of Patent: Dec. 22, 2015

(54) ***CALADIUM* PLANT NAMED 'TIKI TORCH '**

(50) Latin Name: *Caladium×hortulanum*
Varietal Denomination: Tiki Torch

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 201 days.

(21) Appl. No.: 13/998,474

(22) Filed: Nov. 4, 2013

(51) Int. Cl.
*A01H 5/12* (2006.01)

(52) U.S. Cl.
USPC ..... Plt./373

(58) Field of Classification Search
USPC ..... Plt./373
See application file for complete search history.

*Primary Examiner* — Anne Grunberg
(74) *Attorney, Agent, or Firm* — C. A. Whealy

(57) ABSTRACT

A new and distinct cultivar of *Caladium* plant named 'Tiki Torch', characterized by its compact, upright and uniformly mounded plant habit; vigorous growth habit and rapid growth rate; lance-type leaves that have rose red-colored centers and venation with lime green to chartreuse-colored margins; and good landscape performance.

4 Drawing Sheets

Botanical designation: *Caladium×hortulanum.*
Cultivar denomination: 'TIKI TORCH'.

BACKGROUND OF THE INVENTION

The present invention relates to a new and distinct cultivar of *Caladium* plant, botanically known as *Caladium×hortulanum*, commercially referred to as a lance (strap) leaf-type *Caladium* and hereinafter referred to by the name 'Tiki Torch'.

The objective of the Inventor's breeding program is to create new *Caladium* plants that have uniform plant habit, exceptional container and garden performance and attractive and unique leaf coloration.

The new *Caladium* plant originated from a cross-pollination made by the Inventor in April, 2008 in Avon Park, Fla. of *Caladium×hortulanum* 'Highlighter', not patented, as the female, or seed, parent with *Caladium×hortulanum* 'John Peed', not patented, as the male, or pollen, parent. The new *Caladium* plant was discovered and selected by the Inventor as a single plant within the progeny of the stated cross-pollination in a controlled outdoor nursery environment in Zolfo Springs, Fla. on September, 2009.

Asexual reproduction of the new *Caladium* plant by 'chipping' the tubers (cutting the tuber into segments with each segment containing an axillary bud and tuber cortical tissue) in a controlled outdoor nursery environment in Lake Placid, Fla. since April, 2010 has shown that the unique features of this new *Caladium* plant are stable and reproduced true to type in successive generations of asexual reproduction.

SUMMARY OF THE INVENTION

Plants of the new *Caladium* have not been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of 'Tiki Torch'.

These characteristics in combination distinguish 'Tiki Torch' as a new and distinct *Caladium* plant:

1. Compact, upright and uniformly mounded plant habit.
2. Vigorous growth habit and rapid growth rate.
3. Lance-type leaves that have rose red-colored centers and venation with lime green to chartreuse-colored margins.
4. Good landscape performance and relatively tolerant to high light conditions.

Plants of the new *Caladium* differ primarily from plants of the female parent, 'Highlighter', in the following characteristics:

1. Plants of the new *Caladium* are slightly shorter than plants of 'Highlighter'.
2. Plants of the new *Caladium* are faster growing and produce finished plants about one to two weeks earlier than plants of 'Highlighter'.
3. Plants of the new *Caladium* and 'Highlighter' differ in leaf color as leaves of plants of 'Highlighter' are chartreuse to yellow green in color with variable green-colored blotches and flecks.
4. Plants of the *Caladium* and 'Highlighter' differ in leaf petiole coloration.

Plants of the new *Caladium* differ primarily from plants of the male parent, 'John Peed', in the following characteristics:

1. Plants of the new *Caladium* are shorter and more mounded than plants of 'John Peed'.
2. Plants of the new *Caladium* are faster growing and produce finished plants about one to two weeks earlier than plants of 'John Peed'.
3. Plants of the new *Caladium* and 'John Peed' differ in leaf shape and color as leaves of plants of 'John Peed' are fancy-types with dark red-colored centers and dark green-colored margins.
4. Plants of the *Caladium* and 'John Peed' differ in leaf petiole coloration.

Plants of the new *Caladium* can be compared to plants of *Caladium×hortulanum* 'Miss Muffet', not patented. In side-by-side comparisons, plants of the new *Caladium* differed primarily from plants of 'Miss Muffet' in the following characteristics:

1. Plants of the new *Caladium* and 'Miss Muffet' differed in leaf color as leaves of plants of 'Miss Muffet' were pale green in color and tinged with pink with random dark red-colored spots and green to lime green-colored margins.
2. Plants of the new *Caladium* and 'Miss Muffet' differed in leaf petiole color.

Plants of the new *Caladium* can be compared to plants of *Caladium×hortulanum* 'Raspberry Moon', disclosed in U.S. Plant Pat. No. 20,069. In side-by-side comparisons, plants of the new *Caladium* differed primarily from plants of 'Raspberry Moon' in the following characteristics:

1. Plants of the new *Caladium* were shorter and more mounded than plants of 'Raspberry Moon'.
2. Plants of the new *Caladium* produced finished plants about one week later than plants of 'Raspberry Moon'.
3. Plants of the new *Caladium* and 'Raspberry Moon' differed in leaf shape and color as leaves of plants of 'Raspberry Moon' were fancy-types and light green in color with random dark red purple-colored spots and splotches.
4. Plants of the new *Caladium* and 'Raspberry Moon' differed in leaf petiole color.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet is a side perspective view of a typical plant of 'Tiki Torch' in a 15-cm and grown in a shadehouse.

The photograph at the top of the second sheet is a comparison view of typical plants of 'Tiki Torch' grown in 15-cm containers; the plant on the left has not had its tuber de-eyed and the plant on the right has had its tuber de-eyed prior to planting.

The photograph at the bottom of the second sheet is a close-up view of a typical freshly-harvested tuber and roots of 'Tiki Torch' plants.

The photograph on the third sheet is a side perspective view of typical plants of 'Tiki Torch' grown in an open field.

The photograph at the top of the fourth sheet is a comparison view of typical potted plants of the male parent, 'John Peed' (left), 'Tiki Torch' (center) and the female parent, 'Highlighter' (right).

The photograph at the bottom of the fourth sheet is a comparison view of typical potted plants of 'Miss Muffet' (left), 'Tiki Torch' (center) and 'Raspberry Moon' (right).

DETAILED BOTANICAL DESCRIPTION

The aforementioned photographs and following observations and measurements describe plants grown in 15-cm containers in a polypropylene-covered shadehouse (30% light reduction) in Avon Park, Fla. and plants grown in ground beds under full sunlight in an outdoor nursery in Zolfo Springs, Fla. The plants were grown under cultural practices typical of commercial shadehouse and outdoor nursery production. During the production of the plants, day temperatures ranged from about 29° C. to 35° C. (shadehouse) or 28° C. to 33° C. (outdoor nursery), night temperatures ranged from about 23° C. to 26° C. (shadehouse) or 22° C. to 25° C. (outdoor nursery) and light levels were about 8,000 foot-candles (shadehouse) or 10,000 to 12,000 foot-candles (outdoor nursery). Plants grown in the shadehouse were seven weeks old and plants grown in the outdoor nursery were eight months old when the photographs and the detailed description were taken. In the following description, color references are made to The Royal Horticultural Society Colour Chart, 2001 Edition, except where general terms of ordinary dictionary significance are used.

Botanical classification: *Caladium×hortulanum* 'Tiki Torch'.

Parentage:

*Female, or seed, parent.*—*Caladium×hortulanum* 'Highlighter', not patented.

*Male, or pollen, parent.*—*Caladium×hortulanum* 'John Peed', not patented.

Propagation:

*Type.*—By "chipping" the tubers.

*Time to initiate roots, summer.*—About seven to ten days at 32° C.

*Time to initiate roots, winter.*—About two to three weeks at 24° C.

*Tuber description* (*outdoor nursery-grown plants*).—Appearance: Multi-segmented and somewhat flattened; individual segments round to ovate in shape. Height: About 2.2 cm. Diameter: About 2.8 cm. Segment height: About 1.6 cm. Segment diameter: About 1.5 cm. Texture: Thick, starchy; somewhat brittle. Color: Epidermis, freshly-harvested: More brown than 199A to 199B and 200B. Epidermis, dried: Close to 200A to 200B. Cortical tissue: Close to 4C to 4D. Axillary buds: Close to 27D. Root description: Thick, fleshy contractile roots; color, close to 155C. Rooting habit: Medium density.

Plant description:

*Plant type.*—Herbaceous perennial; suitable as a potted plant in containers 15-cm to 25-cm and suitable as a landscape plant in shaded areas.

*Plant and growth habit.*—Compact, upright and uniformly mounded plant habit; vigorous and dense growth habit; rapid growth rate, potted plants in finished or saleable form in about seven weeks after planting tubers; leaf petioles and leaves arise from one or more growing points on tubers; petioles mostly upright and leaning outwardly with development.

*Plant height, from soil level to top of foliar plane, shadehouse-grown potted plants.*—About 15 cm to 18 cm.

*Plant diameter or spread, shadehouse-grown potted plants.*—About 30 cm to 42 cm.

*Number of shoots per plant, shadehouse-grown potted plants.*—About three to five shoots develop per #1 tuber.

*Cataphylls, shadehouse-grown potted plants.*—Length: About 4.6 cm to 6.2 cm. Width: About 1 cm to 1.2 cm. Shape: Wedge-shaped or ligulate. Apex: Obtuse or bluntly acute. Base: Sheathing the stem. Color, inner surface: Close to 196B. Color, outer surface: Close to 199D streaked, stippled and tessellated with close to 177C to 177D; with development, color becoming closer to 199D stained with close to 183D.

Leaf description:

*Arrangement and type.*—Alternate; simple; lance-type.

*Length, shadehouse-grown potted plants.*—About 15 cm to 19 cm.

*Width, shadehouse-grown potted plants, flattened.*—About 10.5 cm to 13.5 cm.

*Shape.*—Ovate.

*Apex.*—Acuminate to acute.

*Base.*—Sagittate to sagittate-peltate.

*Margin.*—Entire; moderately wavy with broad undulations.

*Texture, upper surface.*—Smooth, glabrous; flexible; dull sheen.

*Texture, lower surface.*—Smooth, glabrous; glaucous.

*Venation pattern.*—Pinnate.

*Color, shadehouse-grown potted plants.*—Developing and fully expanded leaves, upper surface: Main colors: Center, close to 181A tinged with close to 53B; towards the margins, close to 147C to 147D tinged with close to 145C; margins, close to 147B to 147C tinged with close to 145C; narrow leaf edge, close to N186C. Basal notch: Close to 181A. Midrib: Close to 53A to 53B. Lateral venation: Primary venation, close to 53A to 53B; secondary venation towards the margins, close to 181A. Developing and fully expanded leaves, lower surface: Main colors: Center, close to 182A; towards the margins, close to 193A to 193B and close to 193A to 193B tinged with close to 182D; margins, close to 191A; narrow leaf edge, close to N186C. Basal notch: Close to 183A. Midrib: Close to 193A mottled with close to 182B. Lateral venation: Primary venation, close to 193A mottled with close to 182B; secondary venation towards the margins, close to 182D.

*Petiole.*—Aspect: Initially upright and straight; with development, leaning outwardly; flexible. Length, shadehouse-grown potted plants: About 12 cm to 14 cm. Diameter, distal, shadehouse-grown potted plants: About 3 mm to 4.8 mm. Diameter, proximal, shadehouse-grown potted plants: About 4 mm to 7 mm. Color, shadehouse-grown potted plants: Just below the leaf and petiole junction: Close to 182C to 182D faintly stippled and streaked with close to 181C. Overall: Close to 182D tinged with close to 177D and close to 147D faintly tessellated, streaked and stippled with close to 177A. Wing length, shadehouse-grown potted plants: About 3.5 cm to 5.2 cm. Wing diameter, shadehouse-grown potted plants: About 5 mm to 7 mm. Wing color, shadehouse-grown potted plants, inner surface: Close to 196B. Wing color, shadehouse-grown potted plants, outer surface: Close to 199D streaked and stippled with close to 177C to 177D.

Inflorescence description: Inflorescence initiation and development have not been observed on plants of the new *Caladium.*

Disease & pest tolerance: Plants of the new *Caladium* have been observed to have above average tolerance to *Xanthomonas* Leaf Spot and to have average tolerance to *Pythium* Root Rot. Plants of the new *Caladium* have not been observed to have resistance to pests and other pathogens common to *Caladium* plants.

Temperature tolerance: Plants of the new *Caladium* have been observed to be tolerant to temperatures ranging from about 7° C. to about 40° C. and are suitable for USDA Hardiness Zones 8A to 11.

It is claimed:

1. A new and distinct *Caladium* plant named 'Tiki Torch' as illustrated and described.

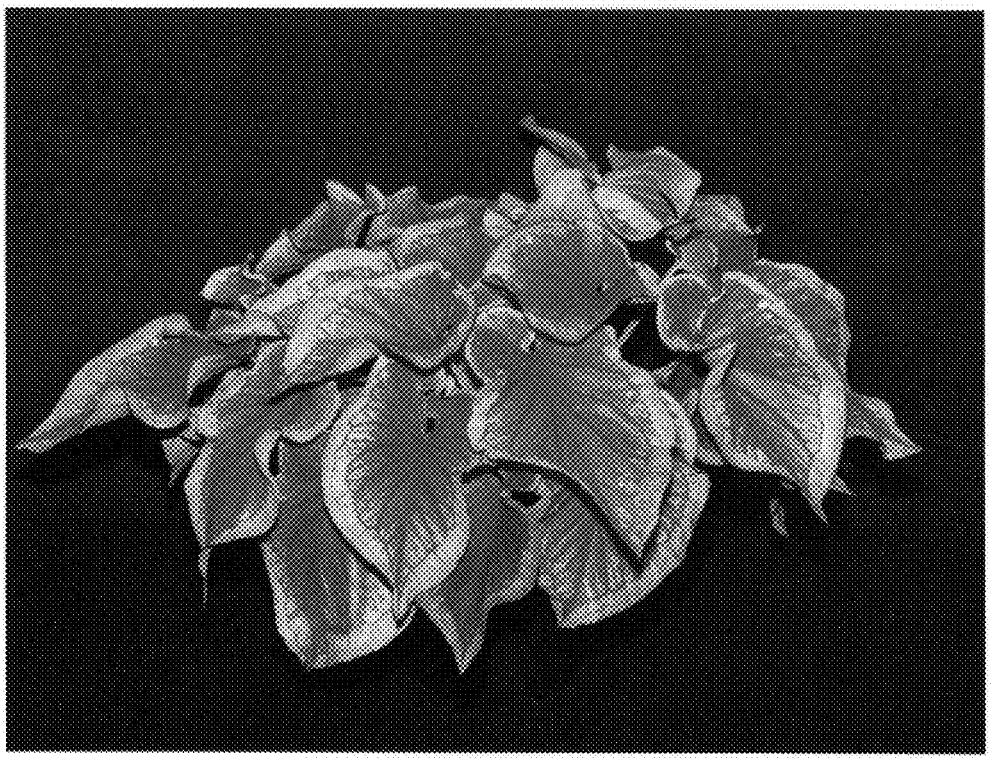

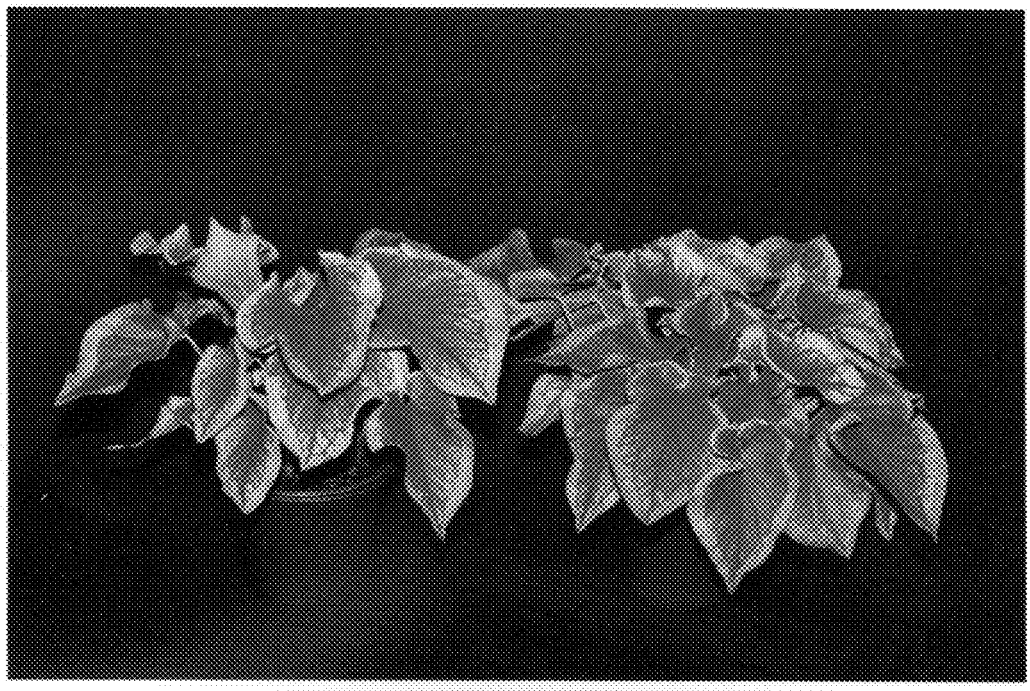
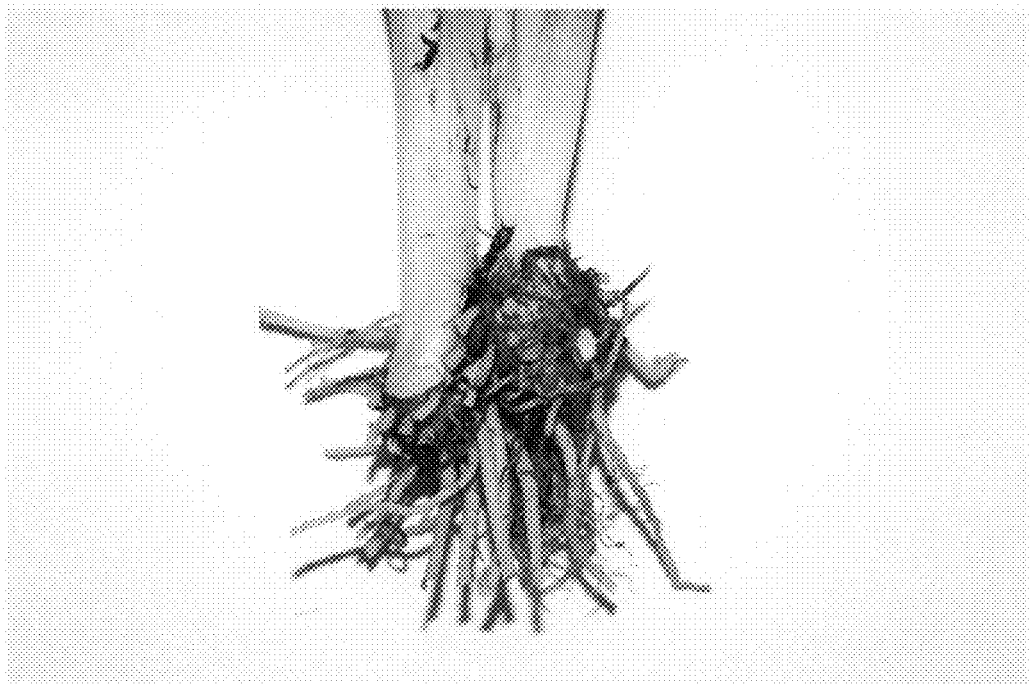

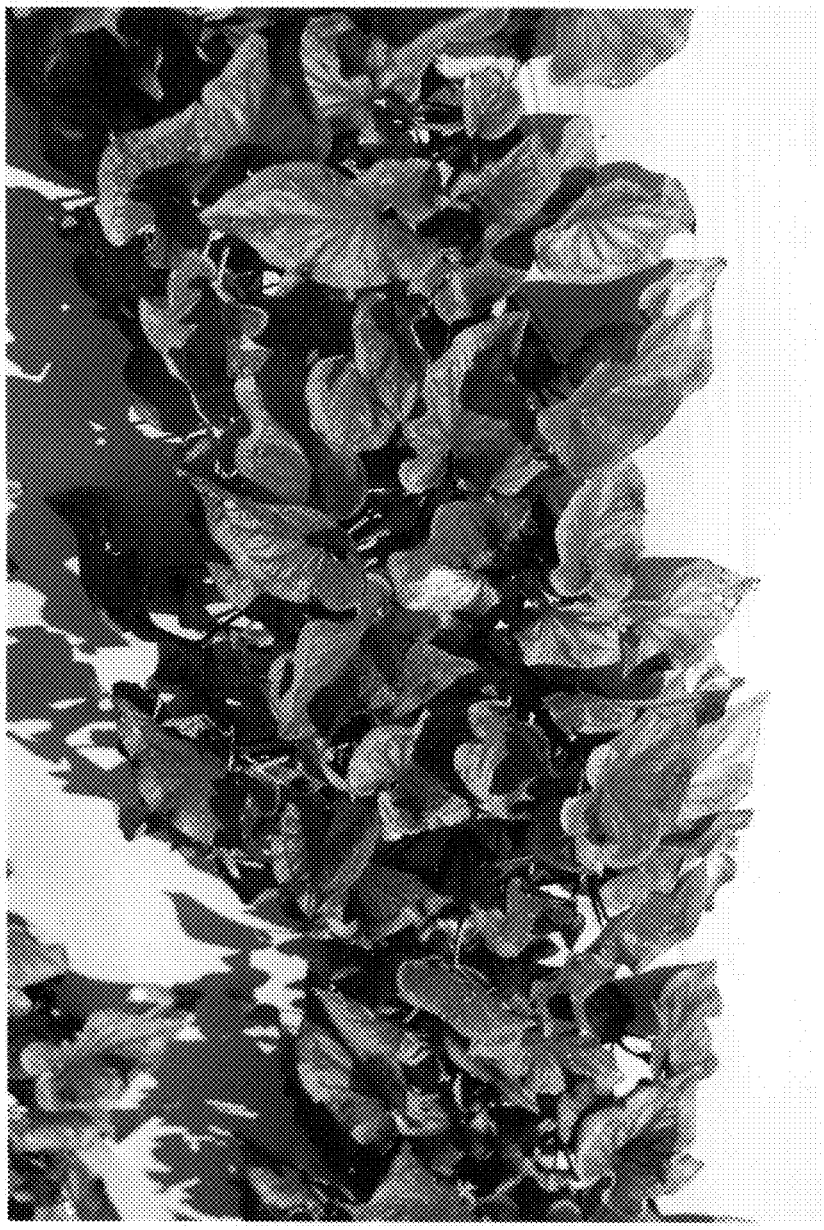

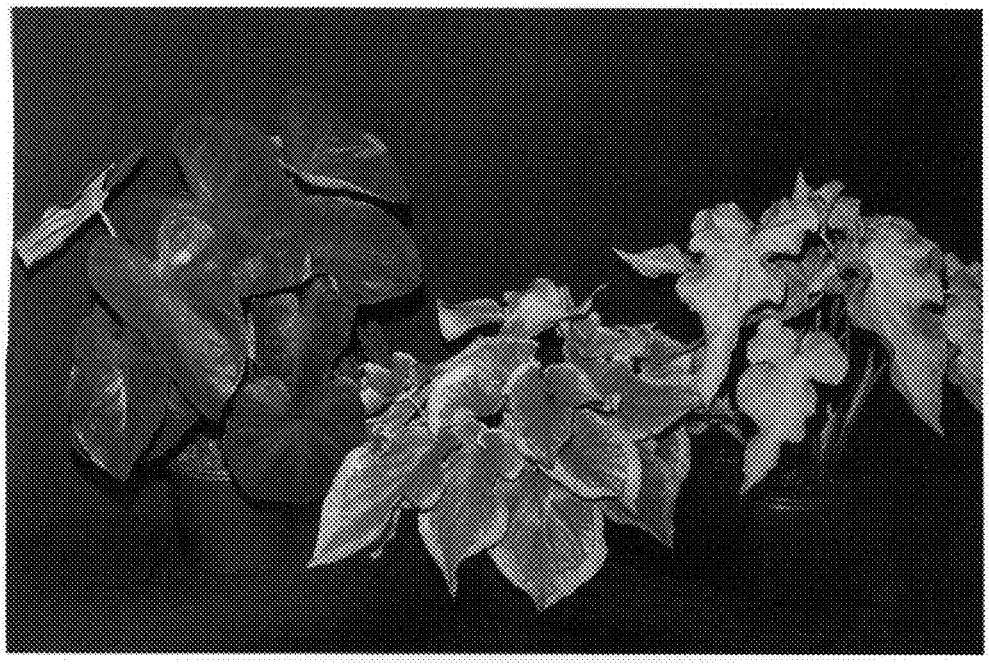
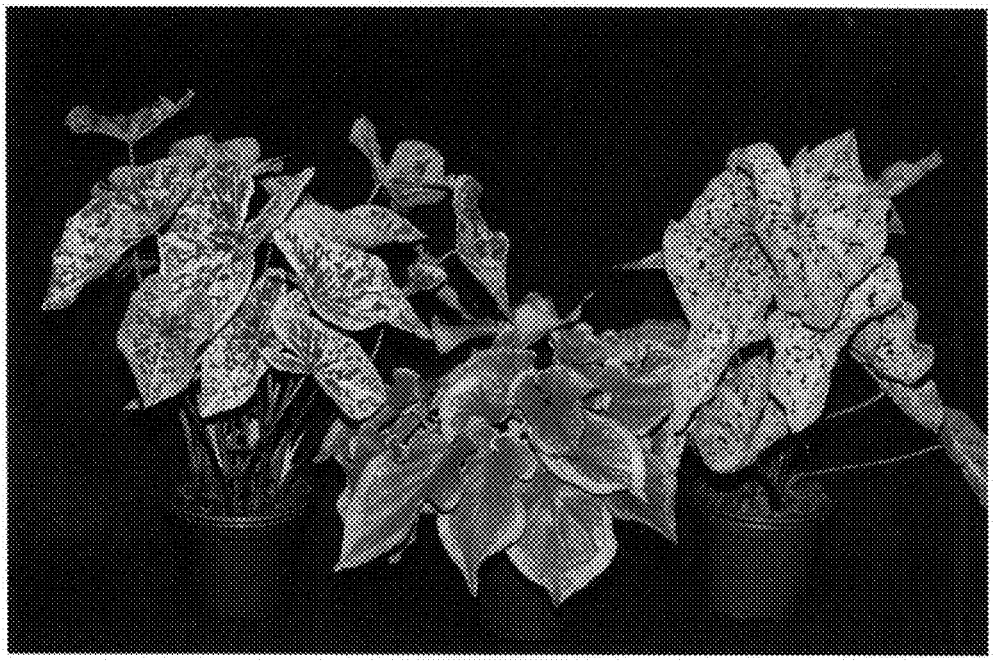

* * * * *